(12) United States Patent
Basu et al.

(10) Patent No.: US 7,371,905 B2
(45) Date of Patent: May 13, 2008

(54) METHOD OF PRODUCING HYDROFLUOROCARBONS

(75) Inventors: Rajat S. Basu, East Amherst, NY (US);
Lawrence F. Mullan, Williamsville, NY (US); Peter H. Scheidle, Wheatfield, NY (US); Steven J. Bass, Lawrenceville, GA (US); Addison M. Smith, Buffalo, NY (US)

(73) Assignee: Honeywell International Inc., Morristown, NJ (US)

( * ) Notice: Subject to any disclaimer, the term of this patent is extended or adjusted under 35 U.S.C. 154(b) by 797 days.

(21) Appl. No.: 10/687,781

(22) Filed: Oct. 17, 2003
(Under 37 CFR 1.47)

(65) Prior Publication Data
US 2006/0129005 A1    Jun. 15, 2006

(51) Int. Cl.
*C07C 17/383* (2006.01)
*C07C 17/093* (2006.01)
*C07C 17/07* (2006.01)

(52) U.S. Cl. ...................... 570/165; 570/169
(58) Field of Classification Search ............... 570/165, 570/169
See application file for complete search history.

(56) References Cited

U.S. PATENT DOCUMENTS

| 5,763,708 | A | * | 6/1998 | Clemmer et al. | ........... 570/169 |
| 5,800,682 | A | | 9/1998 | Cerri et al. | .................. 203/99 |
| 6,365,580 | B1 | * | 4/2002 | Clemmer et al. | ........... 514/134 |

FOREIGN PATENT DOCUMENTS

| WO | WO99/07660 | 2/1999 |
| WO | WO99/50208 | 10/1999 |
| WO | WO02/076915 | 10/2002 |
| WO | WO2004/007410 | 1/2004 |

* cited by examiner

Primary Examiner—Peter O'Sullivan
(74) Attorney, Agent, or Firm—Colleen D. Szuch (57) ABSTRACT

A process for producing fluorinated C1 HFCs comprising fluorinating a reactive organic compound to produce a reaction product comprising at least the desired C1 HFC, unreacted reactive organic compound and a byproduct having a boiling point between the boiling point of said desired hydrofluorocarbon compound and said reactive organic compound; and removing from the reaction product at least a substantial portion of the byproduct to produce a high purity product stream.

21 Claims, 2 Drawing Sheets

FIGURE 4

METHOD OF PRODUCING HYDROFLUOROCARBONS

FIELD OF THE INVENTION

The present invention relates generally to the preparation of fluorocarbons and to the preparation of hydrofluorocarbons, such as difluoromethane.

BACKGROUND OF THE INVENTION

Many techniques are known for the production of hydrofluorocarbons (HFCs) and fluorocarbons (FCs). Certain prior methods involve fluorinating chlorinated organic compounds to produce the desired HFC or FC compounds, and then recovering the desired compounds through distillation. Although both liquid phase and vapor phase processes are available, vapor phase catalytic reactions are preferred in certain applications. For example, in certain difluoromethane (HFC-32) production processes, a chlorinated organic compound, such as, for example, dichloromethane (HCC-30), and a fluorinating agent, such as, for example, hydrogen fluoride (HF), are reacted, usually after preheating, in the presence of a fluorination catalyst to generate a reaction product stream.

The desired HFC or FC compound is recovered by the use of distillation from the reaction product stream, which also contains other materials such as unreacted HF and byproducts of the reaction. Distillation is well known in the art and typically involves the use of distillation means, such as a packed column or one with trays, operated at pressures and temperatures selected to separate the reaction product stream into a stream relatively rich in the desired compound and stream relatively rich in compounds that are not desired in the finished product, such as unreacted components and unwanted byproducts. Distillation pressure and temperature are interrelated such that higher operating pressures generally correspond to higher distillation temperatures. Distillation temperatures dictate the heating and cooling requirements of the fractionation tower.

The desirability of a fluorination process is generally linked to the yield and product purity resulting from the process. For example, if the desired product is the HFC difluoromethane, the amount of such product which is recovered from the reaction product should ordinarily be as high as possible, and the type and amount of impurities contained in the final product stream should be as low as possible. While prior processes have achieved a certain level of success as measured by yield and product purity, applicants have come to appreciate that certain features of the prior art may raise barriers against continuing improvement of product yield and purity.

For example, many prior art methods of producing HFCs and FCs suffer from the problem of catalyst deactivation during fluorination, which leads to lower yields. In an attempt to maintain catalyst activity, a regenerating agent, such as chlorine, is typically co-fed with the reactants into the reactor in a continuous, semi-continuous or batch fashion. Applicants have come to recognize, however, that the addition of chlorine can, in certain circumstances, add to the formation of generally undesirable byproducts, which in turn can have a negative effect on yield and product quality.

SUMMARY OF THE INVENTION

Applicants have discovered that in the production of C1 HFCs and FCs, particularly from chlorinated reactants and particularly when chlorine is used as a catalyst regenerator, certain undesirable chlorine substituted byproducts may be produced and that steps are available to eliminate or reduce the levels of these undesirable byproducts without substantially degrading other characteristics of the process. As used herein, the term "C1" is used for convenience to refer to compounds having a single carbon atom.

Applicants have found that for such processes, particularly for those in which the desired fluorocarbon is HFC-32, the formation of intermediate boiling compounds, particularly chloromethane ($CH_3Cl$ or HCC-40), may occur to a detrimental extent, particularly when the reaction system utilizes a catalyst regenerator such as chlorine. For the purposes of convenience, the term "intermediate boiling" refers to compounds or combinations of compounds that have boiling points which are above the boiling point of the desired HFC but below the boiling point of the reactive organic compound and/or the fluorination agent. Applicants have discovered that in such preferred embodiments the overall process can be improved by reducing the concentration of one or more of the intermediate boiling, chlorinated byproducts, and in particular HCC-40, in the final product stream by: (1) fluorinating a chlorinated reactant to produce a reaction product comprising the desired C1 HFC and/or FC and at least one intermediate boiling, chlorinated C1 by-product, preferably including dichlorodifluoromethane (CFC-12) and/or HCC-40; and (2) removing at least a substantial portion of at least one of said byproducts from said reaction product to produce a product stream having a low concentration of said by-product relative to said reaction product stream. Applicants have found that for such processes, particularly those in which the desired product is HFC-32, the removing step of the present invention preferably comprises: (1) fluorinating the intermediate chlorinated by-product in at least a second reaction stage; (2) removing from the reaction product, preferably by the use of a distillation side stream, a stream relatively rich in the intermediate chlorinated by-product; or (3) combinations of each of steps (1) and (2).

DETAILED DESCRIPTION OF PREFERRED EMBODIMENTS

In preferred embodiments, the present invention provides a process for producing a fluorinated organic compound comprising: (a) fluorinating an organic compound, preferably in the presence of a fluorination catalyst and preferably while maintaining a relatively low reaction pressure, to produce a reaction product comprising at least one desired C1 FC and/or desired C1 HFC and at least one unwanted C1 by-product which has a boiling point between said desired product and said fluorinating agent, or between said desired product and the organic compound being fluorinated, or between said desired product and both the organic compound being fluorinated and the fluorination agent; and (b) removing one or more of the by product(s) from the reaction product.

Figures 1, 2:
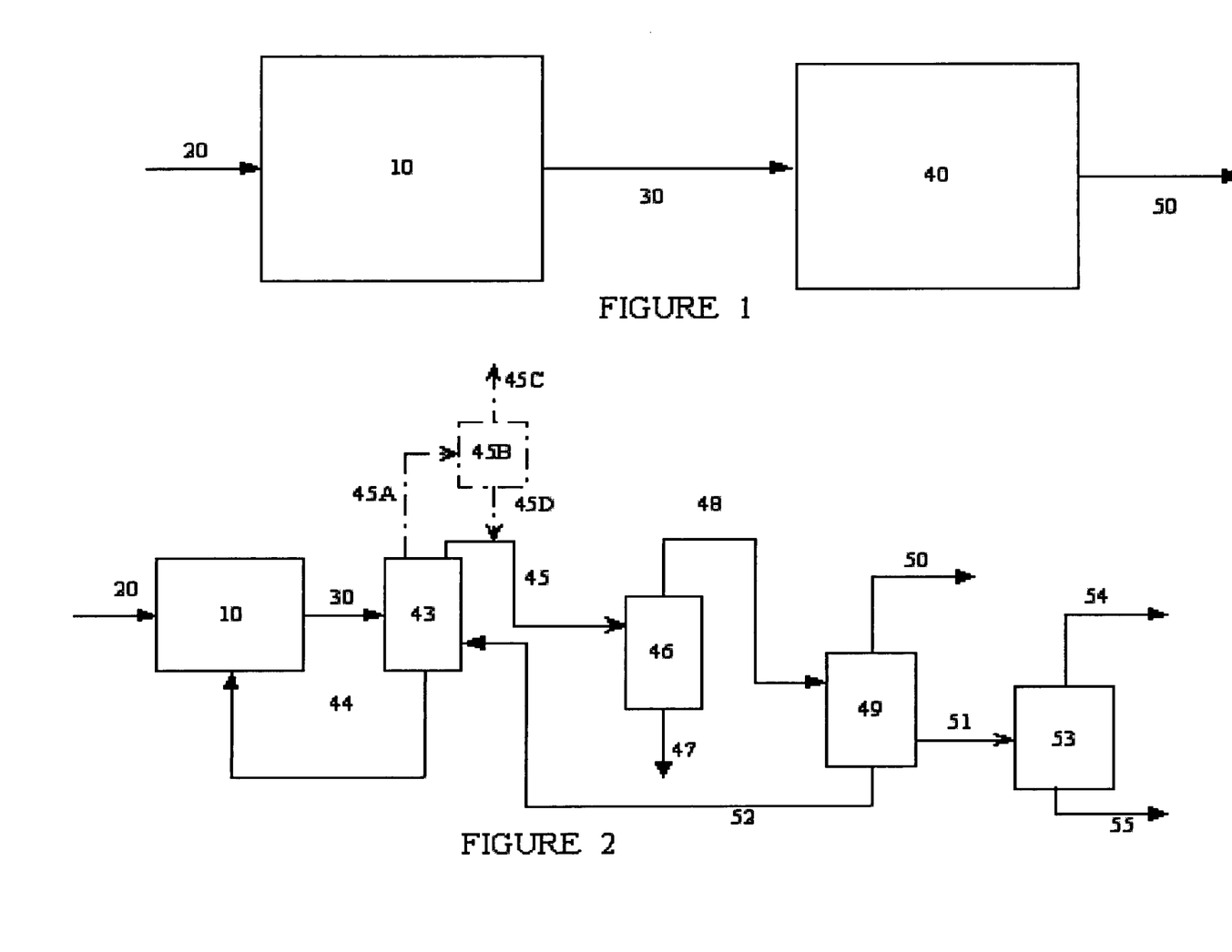
FIG. 1 is a block diagram of the process according to one embodiment of the present invention.
FIG. 2 is a block diagram of a more specific process flow according to an embodiment of the present invention in which a distillation side-stream is used.

With reference now to FIG. 1, the present invention preferably comprises a fluorination step 10 having at least one input stream 20. It will be appreciated by those skilled in the art that the feed stream 20 is illustrated in the figures, as is the case with all of the streams illustrated in the figures, as a single stream for the purposes of convenience only. It will be understood that the stream 20 is intended to encompass and represent not only a single stream but also two or more separate streams which are introduced into the associated unit operation, such as the reaction vessel, at the same or different locations. Furthermore, it will also be appreciated by those skilled in the art that the reaction vessel 10 is illustrated as a single block but is intended to encompass and represent also the possibility of two or more separate vessels or unit operations connected in either a series or parallel configuration, or a combination of series and parallel configurations. Once again, it will also be appreciated that this utilization of the block figures for unit operations is intended to encompass all such combinations throughout the figures.

Exiting from the reaction step 10 is a reaction product stream 30. The reaction product comprises the desired compound and at least one intermediate boiling, chlorinated C1 by-product, preferably CFC-12 and/or HCC-40 and/or combinations of these. The reaction product stream 30 generally will also contain unreacted reactants, catalyst and other byproducts, some of which may also be intermediate boiling compounds.

The reaction product stream is introduced to one or more unit operations, represented by block 40 in FIG. 1, which serve to remove from the reaction product a substantial amount of the aforesaid by-product. The removing step of the present invention thus preferably produces a product stream 50 of desirably high purity and/or desirably high yield of the desired C1 HFC and/or FC. It will be appreciated that there may be one or more other effluent streams (not shown) from the removal step 40, including streams which are recycled back to the fluorination step 10 and/or sent for further processing or disposal.

The Fluorination Step

The fluorination step of the present invention may comprise any one of a large combination of unit operations carried out over a wide range of process conditions, and all such combinations and variations are within the scope of the present invention. In preferred embodiments, the fluorination step comprises a vapor phase fluorination reaction carried out in the presence of a fluorination catalyst. It is also generally preferred that the reaction pressure range, which in turn influences the operating pressure of downstream operations, is selected so as to minimize the formation of unwanted byproducts. More particularly, it is preferred that the reaction pressure range is lower than the pressure conventionally used for high-temperature distillation.

The reaction step preferably comprises introducing into an appropriate reaction vessel or container a fluorination agent and a reactive organic compound. Numerous suitable fluorination agents are known in the art, and all such agents are adaptable for use in the present invention. A preferred fluorination agent that can be mentioned by way of example is hydrogen fluoride (HF), and even more preferably substantially anhydrous hydrogen fluoride (HF). The presence of water in the reaction tends to deactivate certain fluorination catalysts that may be used. The term substantially anhydrous, as used herein, means that the HF contains less than about 0.05 weight % water. In certain preferred embodiments, the HF contains less than about 0.02 weight % water. It should be understood, however, that steps can be taken to compensate for the presence of water in the catalyst, such as by increasing the amount of catalyst used, which would allow the use of HF that is not substantially anhydrous.

The reactive organic compound is any compound which is capable of reacting with a fluorination agent under the reaction conditions to produce a more highly fluorinated compound. In highly preferred embodiments, the reactive organic compound contains a carbon-bonded chlorine or other atom replaceable by fluorine and/or that contains a carbon-carbon unsaturated bond that can be saturated with fluorine. Suitable reactive organic compounds include, for example, hydrochlorofluorocarbons (HCFCs, which are compounds containing carbon, chlorine, fluorine and hydrogen), hydrochlorocarbons (HCCs, which are compounds containing carbon, chlorine and hydrogen) and chlorofluorocarbons (CFCs, which are compounds containing carbon, chlorine and fluorine), chlorocarbons (compounds containing carbon and chlorine) or combinations of any two or more of these. In preferred embodiments, especially those in which the desired fluorinated compound comprises HFC-32, the reactive organic compound comprises an HCC, and even more preferably dichloromethane (HCC-30).

It is contemplated that the ratio of the organic reactant to the fluorination agent can vary widely, and that all such ratios which produce acceptable levels of the desired fluorinated compound are within the scope of the present invention. Generally, it is preferred that a sufficient amount of fluorination agent is present in the reaction medium to provide at least a stoichiometric amount of fluorine required to produce the desired product. In certain embodiments, the use of a relatively large excess of fluorination agent to reactive organic compound results in higher yields and selectivity. Additionally, the use of a large excess of fluorination agent will in some embodiments decrease catalyst deactivation rate and result in less decomposition in preheaters and vaporizers, especially when the reaction is conducted at pressures in excess of 3 atmospheres.

In preferred embodiments directed to the production of HFC-32, and particularly where the fluorination agent comprises HF and the organic reactant comprises HCC-30, the HF to HCC-30 mole ratio is preferably form about 1:1 to about 10:1, and more preferably from about 1:1 to about 4:1. In preferred embodiments, and in particular the preferred methods of producing HFC-32 from the fluorination of HFC-30, an amount of fluorination agent, and preferably HF in excess of the stoichiometric amount of the fluorination agent will also contribute to a reduction in the level of byproducts, including intermediate boiling C1 HCCs and C1 HCFCs such as chlorofluoromethane (HCFC-31) in the reaction product. Such a preferred molar excess may in certain embodiments also improve the conversion rate of the organic compound, which will have the effect of reducing the concentration of unreacted HCC-30 in the reaction product.

The reaction step preferably comprises introducing one or more streams into at least one reactor or reaction vessel to produce a reaction mixture comprising reactive organic compound, fluorination agent, catalyst, the desired fluorine substituted C1 product, and unwanted byproduct. As desired, one or more of the streams which are fed to the reactor may be preheated in one or more vaporizers before being introduced to the reactor. In certain preferred embodiments, the preheating step comprises vaporizing and optionally superheating one or more of the reactants. While the preheat temperatures may vary widely within the broad scope of the present invention, in preferred embodiments, one or more of the reactants are brought to temperature of from about 125° C. to about 400° C., more preferably from about 150° C. to about 350° C., and even more preferably from about 175° C. to about 275° C. In certain highly preferred embodiments, the temperature of the feed stream containing the reactive organic compound is preheated to a temperature of from about 200° C. to about 250° C. before being introduced to the reactor. The vaporizer, as well as other vessels in this process, may be made of any suitable corrosion resistant material.

The reactor is charged preferably with a fluorination catalyst before feeding the reactants to the reactor. The term "fluorination catalyst" as used herein refers to a catalyst, preferably an inorganic metal catalyst, which promotes the desired fluorination reaction, such as a reaction involving the substitution of fluorine for chlorine in a chlorinated organic molecule. Such fluorination catalysts are known to those skilled in the art. Exemplary catalysts include, without limitation, chromium, copper, aluminum, cobalt, magnesium, manganese, zinc, nickel, and iron oxides, hydroxides, halides, oxyhalides and inorganic salts thereof, $Cr_2O_3/Al_2O_3$, $Cr_2O_3/AlF_3$, $Cr_2O_3/carbon$, $CoCl_2CrO_3/Al_2O_3$, $NiCl_2/Cr_2O_3/Al_3O_3$, $CoCl_2AlF_3$ and $NiCl_2/AlF_3$. Additionally, supported metal catalyst such as nickel, cobalt, zinc, iron, and copper supported on chromia, magnesia, or alumina may be used. Such chromium oxide/aluminum oxide catalysts are known and are described, for example, in U.S. Pat. No. 5,155,082, which is incorporated herein by reference. Preferably, chromium oxide, a commercially available catalyst, is used. The chromium oxide may be crystalline or amorphous. Preferably amorphous chromium oxide is used.

Before adding the reactants to the reactor, it may be preferable to pretreat the catalyst chemically and/or physically to create active sites which facilitate a fluorination reaction. For example, the catalyst can be pretreated by calcining it under a flow of inert gas such as nitrogen at a temperature comparable to or higher than that of the fluorination reaction. The calcined catalyst is then preferably exposed to a fluorinating agent alone or in combination with up to about 5 to 99 weight percent of an inert gas at a temperature from about 200° C. to about 450° C. for at least about an hour. Preferably, the catalyst is subjected to a third step in which an oxidation agent, such as chlorine, is contacted with the catalyst to improve its reactive properties further. Preferably, the chlorine is diluted with from about 60 to about 75% HF and/or from about 20 to about 30% of an inert gas. The chlorine may be passed over the catalyst at a total volume chlorine to total volume catalyst ratio of from about 1:4 to about 1:3,000, more preferably from about 1:4 to about 1:100, and even more preferably of about 1:10. Preferred exposure times are from about 1 to about 200 hours, more preferably about 5 to about 70 hours, and even more preferably from about 10 to about 30 hours. The chlorine exposure may be conducted at any temperature and pressure convenient to the fluorination reaction.

The reactants can be fed individually or as a mixture to the reactor and, under the appropriate reaction conditions, will react to form a reaction medium. Once the reaction is under way, the reactants may be continuously added under pressure to supply the additional amounts of reactants needed to continue the process. The feed to the reactor may also include, in addition to fresh reactants, streams which are recycled to the reactor as a result of downstream processing. Such downstream processing can include the removing step of the present invention. Recycle streams which are produced in accordance with preferred embodiments of the present invention are described hereinafter.

The temperature at which the fluorination reaction is conducted and the period of reaction will vary widely, depend on numerous factors, such as the particular staring materials, amounts used, catalyst used, etc, and all such variations are within the scope of the present invention. In view of the teachings and instructions contained herein, one of ordinary skill in the art should be able to adjust readily the condition of the reaction to obtain results desired for any particular application. For embodiments in which the desired fluorocarbon is HFC-32 and the fluorination agent is HF, the preferred reaction temperature is from about 125° C. and about 425° C., more preferably from about 150° C. and about 300° C., and even more preferably from about 200° C. and about 250° C.

Contact times will also vary widely within the scope of the present invention, depending on numerous factors, such as for example, catalyst concentration, the type of catalyst, the reaction temperature and the like. In preferred embodiments, the time required for the reactants to pass through the catalyst bed (assuming a 100% void catalyst bed) is from about 1 to about 120 seconds, more preferably from about 2 to 60 seconds, even more preferably from about 4 to about 50 seconds, and still more preferably from about 5 to about 30 seconds.

The process of the present invention may compromise an optional step in which an oxidizing agent is added to the reaction to regenerate the catalyst. Suitable oxidizing agents are well known in the art. They include, for example, elemental chlorine or oxygen. The oxidizing agent can be added in any suitable way, for example, the oxidizing agent can be added continuously or intermittently, for example, by mixing it with the reactants and feeding it as needed to maintain catalyst activity. In the preferred form, the oxidizing agent is added periodically which reduces the need for monitoring the reaction and the oxidizing feed on a continuous basis. Alternatively or additionally, catalyst activity may be maintained by regenerating the catalyst during periodic shut downs of the reaction. The catalyst does not deactivate as quickly under the preferred operating pressures of the present invention.

As mentioned above, by conducting the reaction at the preferred pressures described herein, the catalyst tends to maintain its activity for a longer period of time than if the reaction is carried out at higher pressures. Accordingly, reduced amounts of oxidizing agent can be used. In certain embodiments this translates into a reduction in the formation of undesirable byproducts. However, even the use of low pressure reaction, alone, does not achieve the desirable results of the present invention. For example, vapor phase production of HFC-32, the amount of HCC-40 which may be found in the reaction product, expressed as a weight percentage based on the combined amount of the desired HFC-32 and the undesired HCC-40 is usually greater than about 0.1%, in some cases greater than about 1%, and even still other cases greater than about 2%. Thus, applicants have found that the fluorination step of the present invention produces a reaction product having significant concentrations of undesirable by products, particularly undesirable chlorinated by products, and most particularly intermediate boiling C1 HCC's.

The amount of undesirable, intermediate-boiling C1 HCC byproducts produced, based on the total organic products in the reaction product, is at least about 0.3 wt %, in some cases at least about 0.5 wt %, and in even other cases at least about 0.8%. In certain embodiments, the intermediate boiling C1 HCC by product in the reaction product consists essentially of HCC-40. In many embodiments of the present invention, the amount of the desired HFC, particularly HFC-32, present in the reaction product is at least about 55%, more preferably at least about 60%, and even more preferably at least about 70% of the total organic compounds in the reaction product.

The Removing Step

The removing step of the present invention comprises one or more unit operations conducted under conditions effective to remove from the reaction product of the present invention chlorine substituted byproducts, more particularly and preferably intermediate boiling C1 HCCs (particularly and preferably chloromethane ($CH_3Cl$ or HCC-40)) and C1 CFCs (particularly and preferably CFC-12). The preferred removal steps of the present invention have been developed, at least in part, as a result of applicants' discovery that such byproducts are produced in detrimental quantities in certain fluorination reactions and that such byproducts generally have a boiling point which is above the boiling point of the desired HFC but below the boiling point of the fluorination agent, and in some cases below the boiling point of the reactive organic compound. The removal step of the present invention, in combination with the fluorination step, can thus result in a process which is unexpectedly superior in both the yield and purity of the desired HFC. Unless specifically indicated to the contrary herein, the term "boiling point" refers to the normal boiling point of the component, that is, the boiling point under standard atmospheric pressure conditions.

Table 1 below identifies some of the compounds which may be found in varying quantities in the reaction product, together with an indication of the normal boiling point of each.

| COMPOUND | BOILING POINT, ° C. |
|---|---|
| HCC-30 ($CH2Cl2$) | 40 |
| HF | 19.5 |
| HCFC-21($CHFCl2$) | 9 |
| HCFC-31 ($CH2FCl$) | −9.1 |
| HCC-40 ($CH3Cl$) | −24.2 |
| FCC-12 ($CCl2F2$) | −29.8 |
| HCFC-22 ($CHClF2$) | −40.8 |
| HFC-32 ($CH2F2$) | −51.6 |
| CFC-13 ($CClF3$) | −81 |
| HFC-23 ($CHF3$) | −82 |

In highly preferred embodiments, the removing step removes at least about 99% and even more preferably at least about 99.99% of the intermediate boiling, C1 HCC (for example HCC-40) by-product contained in the product stream. It is also preferred that the removing step removes at least about 99% and even more preferably at least about 99.99% of the intermediate boiling, C1-CFCs. In view of the teachings contained herein, those skilled in the art will appreciate that the removal step of the present invention has as a primary goal the production of a product stream having a relatively high concentration of the desired product, such as HFC-32 and a relatively low concentration of undesirable byproduct, particularly and preferably HCC-40 and CFC-12. In highly preferred embodiments, therefore, the process of the present invention produces a product stream comprising at least about 99 percent of the desired product HFC-32 and not greater than about 1 percent of the unwanted byproduct HCC-40 and not greater than about 1 percent of the unwanted byproduct CFC-12. In addition, it is generally preferred in such embodiments that at least about 80 percent, more preferably at least about 90 percent and even more preferably at least about 98 percent of the HFC-32 contained in the reaction product, for example, the stream 30 which exits the reaction step 10, is contained in the final product stream, such as the stream 50. In this way, the present invention provides a process capable of achieving high yield, high recovery rate and low impurity level.

Two specific embodiments of the removal step of the present invention are described below. Particularly, described in detail below in connection with the figures are embodiments in which removal is achieved by separation and embodiments in which removal is achieved by fluorination of the unwanted byproduct.

Removal by Separation

In certain preferred embodiments, the removing step of the present invention includes the step of separating from the product stream at least a portion of the intermediate boiling chlorinated C1 by-product. The term "separating from the product stream" is used herein for convenience to refer not only to processes in which byproduct is separated directly from the reaction product stream but also to processes in which byproduct is separated from a portion of the reaction product stream. For example, the effluent from the fluorination reaction vessel 10 may be first processed to remove catalyst or other components from the reaction product, and to perhaps separate even a portion of the byproduct, before the byproduct is subject to further separation in accordance with the present invention. The term "separating from the product stream" is used herein to refer to the cumulative effect of all such unit operations.

In certain preferred embodiments, the separating step comprises one or more distillation steps which produce one or more streams having a ratio of intermediate boiling, C1 HCC by-product to desired product which is relatively high in comparison to the ratio of these compounds in the reaction product stream. The preferred embodiments of the separating step also preferably produce one or more high purity streams in which the ratio of intermediate boiling, C1 HCC by-product to desired product is relatively low in comparison to the ratio in the reaction product stream. For example, in certain preferred embodiments, the removing step comprises removing catalyst from the reaction product stream to produce a stream which, directly or after further processing, is fed to a distillation operation. In certain of such embodiments, the distillation operation comprises a distillation tower, which may be packed, or trayed, or both, having at least one high purity overhead stream relatively rich in the desired product, at least one bottoms stream relatively lean in desired product, and at least one intermediate boiling stream relatively rich in the byproduct. In preferred embodiments, the overhead stream is comprised of the desired HFC, such as HFC-32, in an amount of at least about 99%, more preferably at least about 99.9%, and even more preferably at least about 99.99% based upon that the total of the organic components in the overhead stream. It is also generally preferred that the overhead stream has less than about 1%, more preferably less than about 0.1%, and even more preferably less than t about 0.01% of intermediate boiling C1 HCC and C1-CFC by-product, particularly HCC-40 and CFC-12, based upon that the total of the organic components in the overhead stream.

Applicants note that the intermediate boiling component CFC-12 and the desired HFC-32 form an azeotrope, as is disclosed in U.S. Pat. No. 5,785,822 (Cerri et al), which is incorporated herein by reference. In certain embodiments it may therefore be necessary to incorporate into the present process the step of separating the components of this azeotrope by pressure swing distillation, liquid/liquid phase separation, and/or other techniques known to those skilled in the art.

A preferred process in which at least one of the desired HFCs is difluoromethane (HFC-32) is described in connection with FIG. 2. A reaction vessel 10 receives at least feed stream 20, which preferably comprises a chlorinated C1 reactant, and even more preferably HCC-30, and a chlorinating agent, more preferably HF. It is also generally preferred to introduce into the reaction vessel a stream (not shown) comprising a catalyst activator, preferably chlorine. Of course, those skilled in the art will appreciate that these streams, and any other streams containing compounds to be used in the reaction step, may be combined or mixed and introduced together into the reaction vessel. The reaction vessel also preferably receives one or more recycle streams 44, the origin of which is described specifically hereinafter.

The reaction product stream 30 from the reaction vessel 10 preferably comprises the desired HFC, namely the preferred HFC-32. The amount of HFC-32 in the reaction product stream can vary greatly within the scope of the present invention. It is generally preferred however, that the reaction product effluent from the fluorination reaction comprises at least about 40% by weight of HFC-32, more preferably from about 45 wt % to about 90% HFC-32, and even more preferably from about 50 wt % to about 85 wt % HFC-32. In addition, the reaction product stream of the present invention contains one or more unwanted byproducts, particularly intermediate boiling chlorinated C1 HCC and CFCs, and even more particularly HCC-40 and CFC-12. Once again the amount of such by-product in the product stream can vary widely, and all such amounts are within the scope of the present invention. It is generally preferred however, that the reaction product effluent from the fluorination reaction comprises from about 0.01 to about 2% of HCC-40, and more particularly from about 0.01% to about 1% HCC-40, and from about 0.01 to about 2% CFC-12.

It is expected that in many embodiments the reaction product stream will also contain varying amounts of chlorofluoromethane (HCFC-31), dichlorofluoromethane (HCFC-21), HCFC-22, HFC-23, CFC-13 and HCl, as well as unreacted feeds such as HF and HCC-30.

The reaction product stream 30 which exits from the fluorination step is preferably introduced to a distillation operation 43 wherein a substantial portion of the catalyst, together with certain other heavy products such as HF, HCC-30 and HCFC-21, are separated to form bottom stream 44. Although it is contemplated that the separation step 43 may comprise a wide variety and combination of unit operations, in preferred embodiments the separation step comprises reducing the temperature of the reaction product stream 30, preferably by heat exchange with a relatively cold fluid and/or introducing a stream at a relatively low temperature into a vessel which also receives the reaction product stream 30. Such an operation is sometimes referred to as a quenching step and produces, in addition to the heavies stream 44, an overhead stream 45 containing a large proportion of the desired products as well as a large proportion of the HCl in the reaction stream. The bottom stream 44 is preferably recycled to the fluorination step 10. As will be appreciated by those skilled in the art, the initial separation step, which is preferably carried out in a distillation column, may have associated with it various heating and cooling equipment which operates in accordance with well-known techniques.

Optionally but preferably the processes include a HCl stripping step, as represented in the Figures as unit operation 45B. In such embodiments, the overhead from the distillation column 43, which is represented by dashed line 45A, is introduced to a stripping column in which the overhead stream 45C carries a large portion of the HCl contained in the stream 45A. Such an operation provides the advantage of permitting the possibility of increasing the economic efficiency of the process by producing HCl for sale. The bottom stream 45D from the stripping operation, which has relatively low concentration of HCl, is then combined with any portion of the overhead stream 45 which has not been introduced to the stripper 45B.

The overhead stream 45 from the distillation operation 43 and/or the bottoms streams 45D from the HCl stripper 45B is preferably further processed by introducing same to a scrubber 46, which may also have associated with it various heating and cooling equipment which operates in accordance with well-known techniques. The purpose of the scrubber is to remove from the product stream at least a substantial portion of the acid moieties, a substantial portion of the HF and/or HCl present in the distillation overhead 45. The acid scrubber 46 preferably produces a bottom stream 47 containing a substantial portion of the acid and an overhead stream 48 which preferably contains a substantial portion of the desired product. Acid stream 47 is preferably disposed of or otherwise processed according to techniques well known to those skilled in the art.

The scrubber overhead 48 is preferably introduced to a fractionation step 49, preferably a distillation column which is trayed and/or contains packing and which may have associated with it various heating and cooling equipment which operates in accordance with well-known techniques.

The main function of column 49 is to produce a stream 50 which is relatively high purity in the desired product, particularly HFC-32. In preferred embodiments, product stream 50 comprises from about 99 to about 99.99 weight percent of HFC-32, and even more preferably comprises from about 99.5 to about 99.99 weight percent of HFC-32. It is also highly important in many preferred embodiments that the product stream 50 contains no greater than about 1 weight percent of intermediate boiling C1 CFCs, and even more preferably no greater than about 0.01 weight percent of intermediate boiling C1 HCCs. This is achieved in accordance with the present invention in large part by the provision of a side stream 51 which is configured to withdraw from the distillation column a stream relatively rich in the unwanted byproduct, particularly HCC-40 and CFC-12. In preferred embodiments, side stream 51 comprises from about 50 to about 85 weight percent of HCC-40 and preferably no more than about 15 weight percent of HFC-32. The fractionation column 49 also preferably produces a bottom stream 52 which contains a substantial portion of the heavy components contained in a feed stream 48, and more particularly unreacted HCC-30 and HF. In preferred embodiments, the bottom stream 52 is recycled to the distillation step 43 and performs the function of a quench stream to aid in removal of the catalyst and other heavy components from the reaction product stream 30.

Those skilled in the art will appreciate that side stream 51 can be processed in accordance with any one of several well-known techniques, and all such processing steps are within the scope of the present invention. In preferred embodiments as illustrated in FIG. 2, the side stream 51 is subject to a further separation step. For example, the side stream may be introduced to a fractionation column 53 operated under conditions effective to separate the stream into at least one stream 54 having a by-product concentration which is high relative to the concentration of the feed stream 51 and at least one stream 55 having a low concentration of by-product relative to the feed stream 51. In certain preferred embodiments the steam 55 has a relatively high concentration of components which are desirably recycled to an upstream fluorination step or to some other step upstream in the process. For example, the fractionation column 53 may comprise a simple flash distillation in which the intermediate boiling byproducts are concentrated in overhead stream 54 and heavier components, unreacted HCC-30 and/or HCFC-31, are concentrated in the bottom stream 55. In such embodiments, the bottom stream 55 is preferably recycled to the fluorination step 10 and/or the catalyst stripping step 43 and the overhead stream 54 is preferably sent to an onsite or an off-site operation for further processing, including optionally disposal.

Those skilled in the art will also appreciate that the particular parameters selected for operation of the fractionation steps 49 and 53 may very widely in accordance with the teachings of the present invention, and that all such combinations of parameters are within the scope of the present invention. For example, in view of the teachings contained herein, those skilled in the art should be capable of readily selecting the size and location of the side stream 51 in order to minimize the amount of the byproduct in the overhead stream 50 without otherwise detrimentally impacting the process.

In an alternative, but generally less preferred embodiment of the separation step, the side stream 51 would not be utilized. Instead, bottom stream 52 from the distillation step 49 would be periodically purged in a manner that would effectively reduce the concentration of the byproduct in overhead stream 50.

Removal by Fluorination

Certain embodiments of present invention involve a removing step which comprises fluorinating at least a portion of the unwanted by product, and more particularly fluorinating at least a portion of the intermediate boiling C1 HCC and/or the intermediate boiling C1-CFC by-product contained in the reaction product. For embodiments in which the reaction product contains intermediate boiling C1-CFCs, it is contemplated that in preferred embodiments at least a portion of such C1-CFC by products are also removed by the further fluorination step. Although it is contemplated that the byproduct fluorination step may comprise introducing the reaction product stream into a separate reactor or reaction vessel, those skilled in the art will appreciate that the step of fluorinating the unwanted by-product may comprise utilization of the same reaction vessel as is used in the first fluorination step. In such cases, the second fluorination step comprises exposing the reaction product contained in the reaction vessel to one or more reaction conditions that are different than the reaction conditions in the first fluorination step. Such changed condition or conditions are more favorable to fluorination of one or more the unwanted, intermediate boiling byproducts than the conditions in the first reaction step, thereby creating a second phase or stage of fluorination which achieves removal of at least a portion of the unwanted byproduct.

It is also contemplated that the reaction product maybe exposed to one or more intermediate unit operations prior to the second stage of fluorination as described herein. For example, it is contemplated that in certain embodiments the reaction product may be introduced into a catalyst stripping operation after it exits the first fluorination stage, and then the catalyst-stripped reaction product maybe introduced to a second stage or phase of fluorination in which one or more of the byproducts are fluorinated and thereby removed from the reaction product stream.

The reaction conditions which are used to affect the second stage of fluorination may vary widely within the scope of the present invention, depending upon, among other parameters, the byproduct or byproducts being removed. In certain preferred embodiments, the removing step preferably comprises introducing the reaction product into a second stage of fluorination operated under conditions effective to convert at least a portion, and preferably a substantially portion, and even more preferably a majority of the intermediate boiling C1 HCCs in the reaction product to a more fully fluorinated product. This step effectively removes at least a portion of the unwanted intermediate boiling chlorinated C1 by-product from the product stream.

In preferred embodiments in which the unwanted byproduct is HCC-40, the reaction conditions in the second stage of fluorination are at temperatures higher than 85° C. and pressures higher than 180 psia in presence of excess HF. This may create a very high corrosion environment and may have to done in a PTFE lined reactor.

Figure 3:
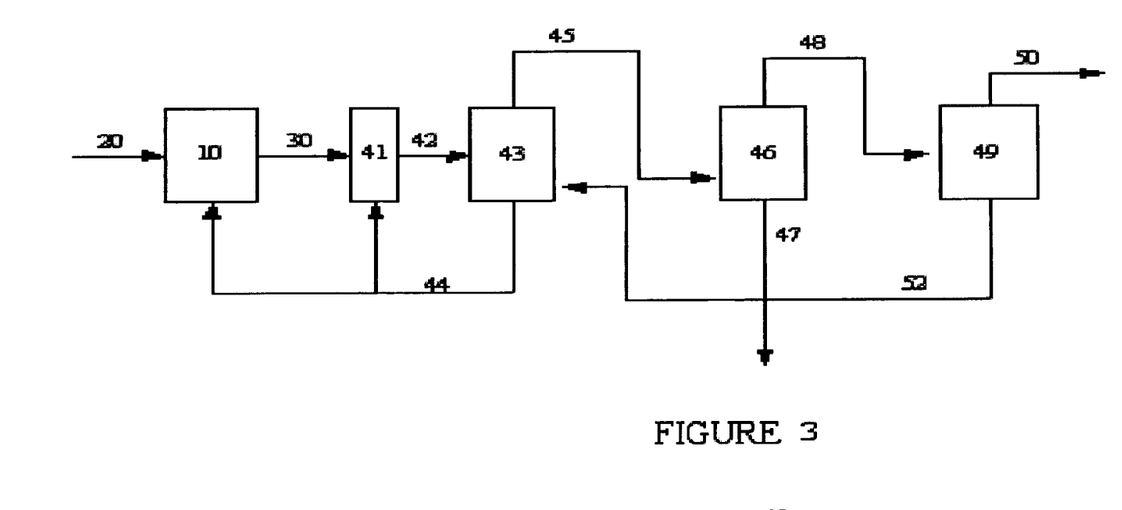
FIG. 3 is a block diagram of a more specific process flow according to an embodiment of the present invention in which a second stage of fluorination is used.

With reference now to FIG. 3, the process flow configuration for certain preferred embodiments which utilize a second stage of fluorination as part of the removal step is shown schematically. More particularly, a feed stream 20 is introduced to a fluorination reaction step 10, which in turn produces a reaction product stream 30. The reaction product stream 30 is then fed to a second stage of fluorination 41 wherein at least a portion of the unwanted intermediate boiling C1 HCC is fluorinated and thereby effectively removed from the reaction product stream 30. The output from this second fluorination stage comprises stream 42. In certain embodiments, such second fluorination stage is all that is required for the removal step. However, in the process illustrated in FIG. 3, the reaction product stream 42 is subject to additional unit operations in order to improve the ultimate purity and/or yield of the final product stream. More particularly, the product stream 42 which exits from the second stage of fluorination is preferably treated in substantially the same manner as is described above in connection with the unit operations 43, 45B and 46. Unit operation 49 may be operated differently in that no intermediate stream is used to remove byproduct from the fractionation column. In addition, the bottoms stream 44 from stripper 43 may be recycled to either the first stage of fluorination 10, the second stage of fluorination 41, or both.

Figure 4:
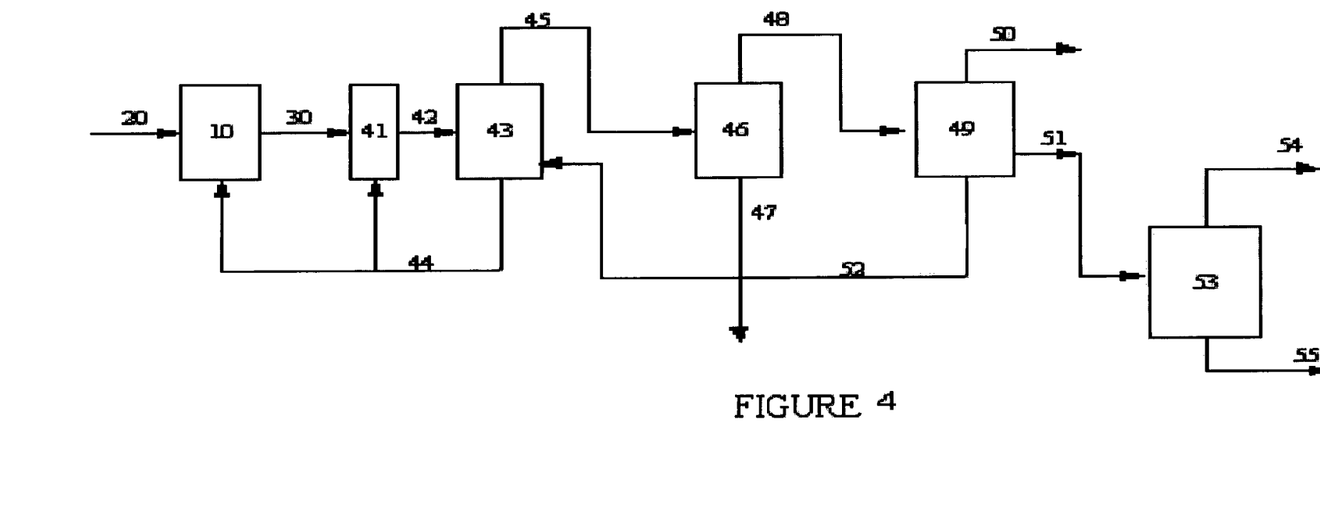
FIG. 4 is a block diagram of a more specific process flow according to an embodiment of the present invention in which a second stage of fluorination is used and in which a distillation side-stream is used.

In certain preferred embodiments, the removing step comprises a combination of a further fluorination step and a separating step in accordance with the present invention. One example of such an embodiment is illustrated in FIG. 4, in which like elements are numbered the same as in the Figures heretofore described. Of course the optional HCl stripper 43B disclosed in FIG. 2 may also be added to the process of FIG. 4.

EXAMPLES

The examples described below are illustrative of the practice of certain embodiments of the invention but are not intended to be necessarily limiting of the broad scope of the invention.

Example 1

A process flow substantially in accordance with that illustrated in FIG. 2 is provided. A reaction vessel 10 is charged with chromium oxide catalyst. The catalyst is subject to standard pretreatment processes, which includes the introduction of chlorine to the catalyst bed for approximately 24 hours.

At substantially steady state conditions, a feed stream 20 consisting of approximately 1.2 lbs/hr of HCC-30 and about 0.6 lbs/hr of HF are introduced to the reactor 10 after being preheated to a temperature of about 260 C to form a vapor phase feed stream. The preheated stream is continuously introduced to the reactor which is maintained at a pressure of about 75 psig to form a vapor phase reaction. Also introduced to the reactor is a recycle stream 44 at the rate and having the composition described in Table 2. The average residence time in the reactor is about 30-45 sec and the average reaction temperature is about 257 C. Chlorine is added to the reactor in amounts and at times sufficient to maintain catalyst activity.

About 85% to about 95% of the HCC-30 is converted to HFC-32, based on the fresh feed to the reactor, to produce a reaction product stream 30. The reactor effluent is then processed sequentially in a distillation column and in an acid scrubber to produce the stream 45.

As can be seen from this example, a product stream having a purity of at least about 99.0 wt % can be produced in accordance with the separation embodiments of the present invention. In addition, the ultimate recovery of HFC-32 from the reactor effluent is also relatively high. More particularly, approximately 95 percent of the HFC-32 contained in stream 30 is contained in the high purity product stream 50.

What is claimed is:

1. A process for producing a desired hydrofluorocarbon compound having a single carbon atom comprising:
   fluorinating a reactive organic compound to produce a reaction product comprising at least the desired hydrofluorocarbon compound, unreacted reactive organic compound and a hydrofluorocarbon byproduct having a boiling point between the boiling point of said desired hydrofluorocarbon compound and said reactive organic compound, wherein said reaction product comprises at least about 0.3 percent by weight of intermediate-boiling C1 HCC byproducts; and
   removing from said reaction product at least a substantial portion of said byproduct to produce a product stream comprising no more than about 2% by weight of said byproduct.

2. The process of claim 1 wherein said desired hydrofluorocarbon is difluoromethane (HFC-32).

3. The process of claim 2 wherein said reaction product comprises at least about 55 percent by weight of HFC-32 based on the total organics in the reaction product.

4. The process of claim 3 wherein said reaction product further comprises at least about 0.3 percent by weight of chloromethane (HCC-40).

5. The process of claim 4 wherein said removing step removes at least about 99 percent by weight of the HCC-40 contained in said reaction product.

6. The process of claim 5 wherein said removing step produces a product stream comprising at least about 99 percent by weight of HFC-32 and not greater than about 1 percent by weight of HCC-40.

7. The process of claim 6 wherein at least about 80 percent by weight of the HFC-32 contained in the reaction product is contained in said product stream.

8. The process of claim 6 wherein at least about 98 percent by weight of the HFC-32 contained in the reaction product is contained in said product stream.

9. The process of claim 1 wherein said removing step comprises separating from said reaction product at least a portion of the intermediate-boiling chlorinated C1 by product.

10. The process of claim 9 wherein said separating step comprises at least one distillation step.

11. The process of claim 10 wherein said at least one distillation step comprises providing a distillation tower having at least one high purity stream relatively rich in said desired hydrofluorocarbon compound, at least one stream relatively lean in said desired hydrofluorocarbon compound, and at least one intermediate boiling stream relatively rich in said intermediate-boiling chlorinated C1 by product.

12. The process of claim 11 wherein said at least one high purity stream relatively rich in said desired hydrofluorocarbon compound is an overhead stream comprising at least about 99 percent by weight of HFC-32 based on the total weight of organics in said overhead stream and wherein said at least one intermediate boiling stream comprises at least about 50 percent by weight of said intermediate-boiling chlorinated C1s.

13. The process of claim 11 wherein said overhead stream comprises at least about 99.8 percent by weight of HCC-32 based on the total weight of organics in said overhead stream and wherein said at least one intermediate boiling stream comprises at least about 50 percent by weight of HCC-40.

14. The process of claim 1 wherein said removing step comprises fluorinating at least a portion of said hydrofluorocarbon byproduct.

15. A process for producing difluoromethane (HFC-32) comprising:
   reacting in at least a first vapor phase reaction stage a chlorine substituted single carbon compound with a fluorination agent comprising hydrogen fluoride in the presence of a fluorination catalyst to produce a reaction product comprising difluoromethane, unreacted chlorine substituted single carbon compound, fluorinating agent and chloromethane (HCC-40);
   separating said reaction product stream into at least a first stream relatively rich in difluoromethane and a second stream relatively rich in unreacted chlorine substituted single carbon compound; and
   reducing the concentration of chloromethane in said reaction product stream by one or more steps selected from the group consisting of:
   (i) fluorinating said chloromethane in at least a second reactor stage;
   (ii) separating from said reaction product stream a third stream relatively rich in said chloromethane; and
   (iii) combinations of (i) and (ii).

16. A process for producing difluoromethane (HFC-32) comprising:
   reacting dichloromethane in at least a first catalytic, vapor phase reactor at a pressure of less than about 100 psig with a fluorination agent comprising hydrogen fluoride to produce a reaction product stream containing difluoromethane, unreacted dichloromethane, fluorination agent and byproduct comprising at least chloromethane; and
   removing from said reaction product at least a substantial portion of said chloromethane to produce a first stream relatively rich in said difluoromethane, a second stream relatively rich in said unreacted dichloromethane, and a third stream relatively rich in said chloromethane.

17. The process of claim 16 wherein said removing step comprises at least one distillation step.

18. The process of claim 17 wherein said at least one distillation step comprises providing a distillation tower having an overhead stream relatively rich in said HFC-32, a bottoms stream relatively lean in said HFC-32, and at least one intermediate boiling stream relatively rich in said chloromethane.

19. The process of claim 18 wherein said overhead stream comprises at least about 99 percent by weight of HFC-32 based on the total weight of organics in said overhead stream and wherein said at least one intermediate boiling stream comprises at least about 50 percent by weight of chloromethane.

20. The process of claim 19 wherein said overhead stream comprises at least about 99.8 percent by weight of HFC-32 based on the total weight of organics in said overhead stream.

21. The process of claim 20 wherein said removing step further comprises fluorinating at least a portion of said chloromethane.

* * * * *